United States Patent [19]
Dessau et al.

[11] Patent Number: 5,939,597
[45] Date of Patent: Aug. 17, 1999

[54] FLUID BED PROCESS FOR PARA-XYLENE PRODUCTION

[75] Inventors: Ralph M. Dessau, Edison; David H. Olson, Pennington, both of N.J.; Robert A. Ware, Wyndmoor, Pa.; Sadi Mizrahi, Cherry Hill, N.J.

[73] Assignee: Mobil Oil Corporation, Fairfax, Va.

[21] Appl. No.: 08/954,787

[22] Filed: Oct. 21, 1997

Related U.S. Application Data

[63] Continuation-in-part of application No. 08/685,272, Jul. 23, 1996, abandoned, which is a continuation of application No. 08/337,657, Nov. 10, 1994, abandoned.

[51] Int. Cl.⁶ .................................................... C07C 2/66
[52] U.S. Cl. ............................................ 585/447; 585/467
[58] Field of Search ...................................... 585/447, 467

[56] References Cited

U.S. PATENT DOCUMENTS

| | | | |
|---|---|---|---|
| 2,904,607 | 9/1959 | Mattox et al. | 585/467 |
| 3,251,897 | 5/1966 | Wise | 585/455 |
| 3,751,504 | 8/1973 | Keown et al. | 585/323 |
| 3,751,506 | 8/1973 | Burress | 585/454 |
| 3,965,207 | 6/1976 | Weinstein | 585/454 |
| 3,965,209 | 6/1976 | Butter et al. | 585/454 |
| 4,002,697 | 1/1977 | Chen | 585/454 |
| 4,049,738 | 9/1977 | Young | 585/447 |
| 4,067,920 | 1/1978 | Kaeding et al. | 585/467 |
| 4,158,024 | 6/1979 | Kaeding et al. | 585/467 |
| 4,444,989 | 4/1984 | Herkes | 585/467 |
| 4,508,836 | 4/1985 | Haag et al. | 502/53 |
| 4,761,513 | 8/1988 | Steacy | 585/467 |
| 4,843,057 | 6/1989 | D'Amore et al. | 502/263 |
| 4,935,574 | 6/1990 | D'Amore et al. | 585/467 |
| 5,349,113 | 9/1994 | Chang et al. | 585/475 |
| 5,349,114 | 9/1994 | Lago et al. | 585/475 |
| 5,395,513 | 3/1995 | Chin et al. | 208/135 |

*Primary Examiner*—Walter D. Griffin
*Attorney, Agent, or Firm*—Peter W. Roberts; Malcolm D. Keen

[57] ABSTRACT

Para-xylene is produced by toluene methylation by charging toluene and a methylating agent to a fluidized bed of catalyst at a rate sufficient to maintain the fluidized bed in a turbulent sub-transport flow regime, reacting the toluene with the methylating agent, and recovering para-xylene from the fluidized bed. The fluidizable catalyst is a microporous material having a Constraint Index of about 1 to about 12. The relative concentration of the catalyst particles having a major dimension of less than 40 microns is controlled at between about 5 and 35 weight percent. The catalyst particles have an apparent particle density of about 0.9 to 1.6 grams per cubic centimeter, a size range of about 1 to 150 microns, and average particle size of about 20 to 100 microns.

10 Claims, 1 Drawing Sheet

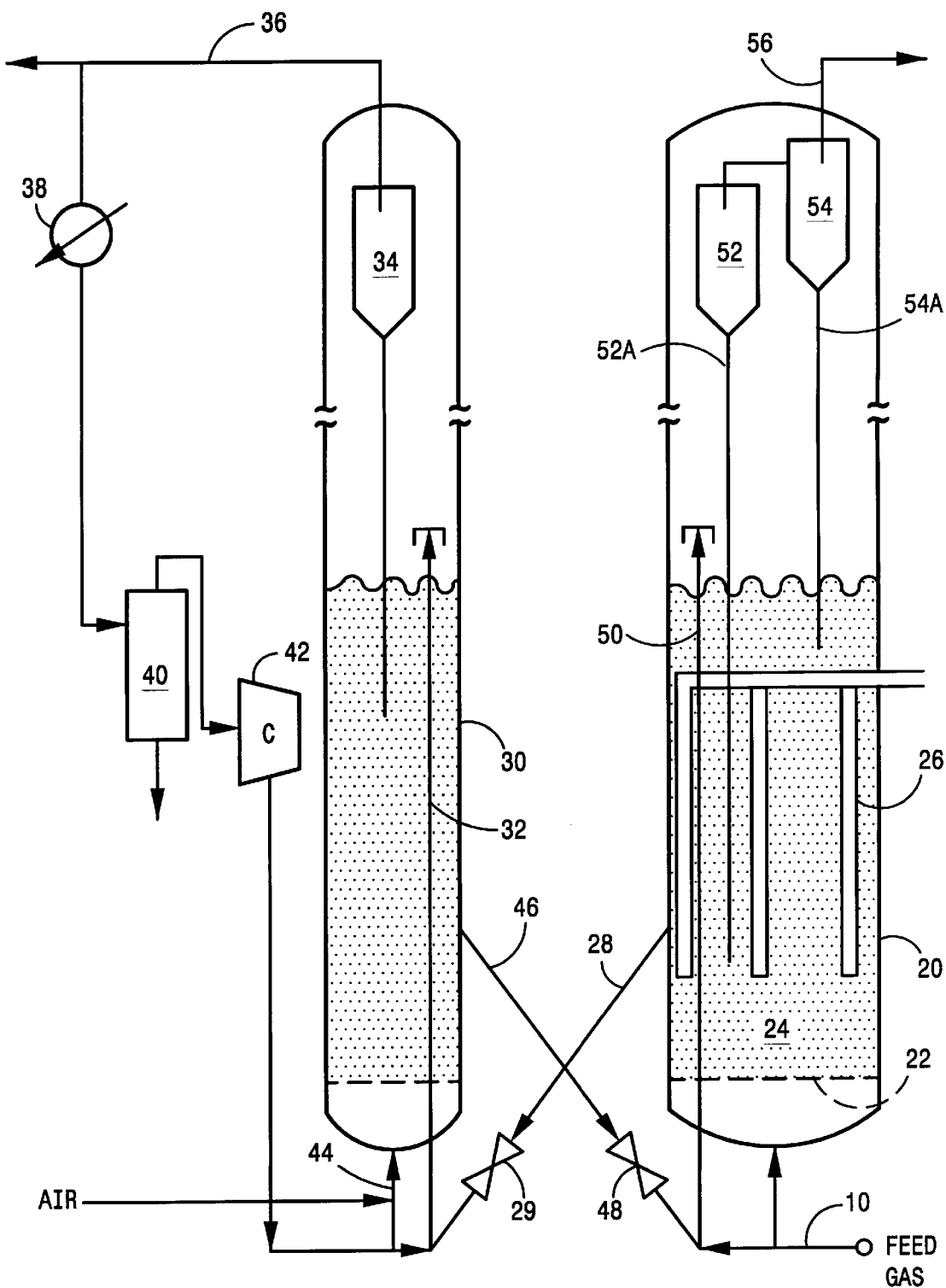
*FIGURE*

5,939,597

FLUID BED PROCESS FOR PARA-XYLENE PRODUCTION

This application is a continuation-in-part of U.S. Ser. No. 08/685,272, now abandoned, filed Jul. 23, 1996 which in turn is a continuation of U.S. Ser. No. 08/337,657 filed Nov. 10, 1994, now abandoned.

FIELD OF THE INVENTION

This invention relates to a fluid bed process for the selective production of para-xylene by catalytic methylation of toluene.

BACKGROUND OF THE INVENTION

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275° C., with the maximum yield of para-xylene in the mixture of xylenes, i.e. about 50 percent of the xylene product mixture, being observed at 225° C. Higher temperatures were reported to result in an increase in the yield of meta-xylene and a decrease in production of para and ortho-xylenes.

While the above-noted prior art is considered of interest in connection with the subject matter of the present invention, the methylation process described herein utilizing a finely divided solid catalyst which has a controlled particle size distribution and which is fluidized in a turbulent sub-transport regime to achieve unexpectedly high selectivity for the production of para-xylene and a high efficiency for the utilization of the methanol alkylating agent has not, insofar as is known, been heretofore described.

Of the xylene isomers, e.g. ortho-, meta- and para-xylene, the latter is of particular value being useful in the manufacture of terephthalic acid which is an intermediate in the manufacture of synthetic fibers such as Dacron brand fiber available from the DuPont de Nemours Company of Wilmington, Del. Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

U.S. Pat. Nos. 3,965,209 to Butter et al. and 4,067,920 to Kaeding teach processes for producing para-xylene in high yield by reaction of toluene with methanol. The reaction is exothermic, generating about 16.5 kcal/mol (280 Btu/lb) of para-xylene produced. The use of steam co-feed (U.S. Pat. Nos. 4,935,574 and 4,843,057 to D'Amore et al.) or multiple reaction beds with interstage methanol addition (U.S. Pat. No. 4,761,513 to Steacy) have been disclosed as means to quench the reaction exotherm and to improve operability of a fixed-bed process.

Under typical reaction conditions the process is also prone to rapid catalyst deactivation. The use of hydrogen co-feed (U.S. Pat. No. 4,444,989 to Herkes) has been disclosed to reduce coking. Kaeding (U.S. Pat. Nos. 4,067,920 and 4,158,024 to Kaeding) discloses the use of a fluidized catalyst zone but with no teaching of controlling the fluidization regime and the catalyst particle size distribution to enhance para-xylene selectivity and methanol utilization efficiency.

SUMMARY OF THE INVENTION

The present invention employs a fluid bed reactor operated under closely controlled conditions of fines content, superficial velocity, and pressure to maintain the fluid bed below transport velocities, in the turbulent regime. Under these conditions, the exothermicity of the reaction is easily controlled and high catalyst activity and selectivity for production of desired products is maintained by withdrawing aged catalyst from the reaction zone, restoring activity by regeneration in a regeneration zone, and returning catalyst to the reaction zone.

The invention resides in a process for the selective production of para-xylene which comprises:

(a) providing a fluidizable catalyst comprising a microporous material having a Constraint Index of from about 1 to about 12;

(b) controlling the relative concentration of catalyst particles having a major dimension of less than 40 microns at between about 5 and 35 weight percent, said catalyst particles having an apparent particle density of about 0.9 to 1.6 grams per cubic centimeter and a size range of about 1 to 150 microns, and an average catalyst particle size of about 20 to 100 microns;

(c) charging toluene and a methylating agent to said fluidized bed at a rate sufficient to maintain said fluid bed in a turbulent sub-transport flow regime; and (d) reacting said toluene with said methylating agent and recovering para-xylene from said fluidized bed.

Preferably, the relative concentration of catalyst particles having a major dimension of less than 40 microns is between about 10 and 25 weight percent.

DESCRIPTION OF THE DRAWING

The FIGURE is a schematic diagram of a fluidized bed reactor system useful in the present invention.

DETAILED DESCRIPTION

The present invention improves control of catalyst activity and conversion of feedstocks to desired product in a process for producing para-xylene from toluene by charging the toluene and the methylating agent to a fluidized bed of catalyst which is maintained in a turbulent sub-transport fluidization regime.

U.S. Pat. Nos. 4,746,762 to Avidan et al., 4,827,069 to Kushnerick et al. and 5,012,026 to Avidan et al. teach sub-transport fluidization of finely divided catalyst particles and is incorporated by reference as if set forth at length herein.

The superficial vapor velocity required to maintain a turbulent sub-transport fluidization regime is dependent on the operating pressure of the system. However, under optimized conditions for the production of para-xylene, in which the operating pressure is about 170–790 kPa (10–100 psig), the turbulent bed has a superficial vapor velocity of about 0.3 to 2 meters per second (m/sec). At higher velocities entrainment of fine particles may become excessive and beyond 10 m/sec the entire bed may be transported out of the reaction zone. At lower velocities, the formation of large bubbles can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 600 kg/m$^3$, and is preferably maintained at an operating density of about 300 to 500 kg/m$^3$, measured at the bottom of the reaction zone, becoming less dense toward the top of the reaction zone due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing catalyst particles having a clean apparent density of 1.06 gm/cc and packed density of 0.85, an average fluidized bed density of about 300 to 400 kg/m$^3$ is satisfactory. By virtue of the turbulence experienced in the turbulent regime, gas-solid contact in the catalytic reactor is improved, providing enhanced activity and para-xylene yield. One main feature of this concept is the inherent control of bubble size and characteristic bubble lifetime. Bubbles of the gaseous reaction mixture are small, random and short-lived, thus resulting in good contact between the gaseous reactants and the solid catalyst particles.

The microporous materials described above must be present within the reaction zone in a form which is readily fluidizable. This result is most preferably achieved by compositing the microporous material with an inert or catalytically active binder such that the resulting composite catalyst particles are characterized by a combination of size, shape, and density as to be classified as Geldart Type A powders. Suitable binders include materials such as clays, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia, and silica-magnesia-zirconia.

For a discussion of fluidization in the Geldart Type classification system, see U.S. Pat. Nos. 4,513,160 to Avidan, 5,012,026 to Avidan et al., as well as Geldart 7 Powder Technology 285 (1973), all of which are incorporated by reference as if set forth at length herein. Briefly, a Geldart Type A powder is a finely divided, easily fluidizable solid.

In particular, the particle size distribution and density of the catalyst composition used in the process of the invention are controlled so that the relative concentration of catalyst particles having a major dimension of less than 40 microns is between about 5 and 35 weight percent, preferably between 10 and 25 weight percent, and so that the catalyst particles have an apparent particle density of about 0.9 to 1.6 grams per cubic centimeter, a size range of about 1 to 150 microns and an average particle size of about 20 to 100 microns.

The process step of reacting toluene with a methylating agent in the present invention is typically carried out at a temperature between about 300° and 750° C., a pressure of between about 101–7000 kPa (0–1000 psig), a weight hourly space velocity between about 0.5 and about 1000 employing a molar ratio of methylating agent to toluene of less than about about 5.

CATALYSTS

The members of the class of microporous materials useful as catalysts in the present invention have an effective pore size of generally from about 5 to about 8 Angstroms or larger, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the microporous crystalline material is not of the desired type. Windows of 10-membered rings are preferred, although, in some instances, excessive puckering of the rings or pore blockage may render these microporous materials ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular microporous crystalline material solely from theoretical structural considerations.

A convenient measure of the extent to which a microporous crystalline solid provides control to molecules of varying sizes to its internal structure is the Constraint Index of the solid. The method by which the Constraint Index is determined is described in U.S. Pat. No. 4,016,218, incorporated herein by reference for details of the method. U.S. Pat. No. 4,696,732 discloses Constraint Index values for typical materials and is incorporated by reference as if set forth at length herein.

In a preferred embodiment, the microporous material of the catalyst is a zeolite having a Constraint index of between about 1 and about 12 and, preferably, a silica/alumina ratio in excess of 30. Examples of such zeolite catalysts include ZSM-5, ZSM-11, ZSM-12, ZSM-22, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

MCM-22 is disclosed in U.S. Pat. Nos. 5,304,698 to Husain, 5,250,277 to Kresge et al., 5,095,167 to Christensen, and 5,043,503 to Del Rossi et al., which patents are incorporated by reference as if set forth at length herein.

Additional molecular sieves which find utility in conjunction with the present invention include pillared silicates and/or clays; aluminophosphates, e.g. ALPO-5, VPI-5; silicoaluminophosphates, e.g. SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875; and 4,742,033. The layered material MCM-36, as described in U.S. Pat. No. 5,304,698 to Husain, is also useful in the present invention.

Many zeolite-containing composite catalysts can be modified or selectivated to improve para-xylene yields from toluene alkylation. The term "selectivation" as used herein refers to steps including coking, steaming, or depositing chemical species (such as Si, P, Mg, or B) to enhance the selectivity of a catalyst for producing para-xylene by alkylating toluene. For example, U.S. Pat. No. 3,965,209 to Butter et al. teaches a method for steaming a catalyst containing a medium-pore zeolite to improve its para-xylene selectivity. U.S. Pat. No. 4,158,024 to Kaeding et al. teaches a method for improving the para-xylene selectivity of a toluene alkylation process by adding at least 0.5 weight percent magnesium to the catalyst which contains a medium-pore zeolite. U.S. Pat. No. 4,554,394 to Forbus et al. teaches a method for treating modified ZSM-5 zeolite-containing catalysts with a vapor phase organophosphorus reagent such as trimethylphosphite or dimethylmethylphosphonate in order to improve the para-selective properties of such catalysts for the conversion of aromatic materials.

In a preferred embodiment, the composite catalyst contains from about 0.5 to about 20 weight percent phosphorus, more preferably from about 1 to about 10 weight percent phosphorus, and most preferably from about 1 to about 5 weight percent phosphorus. In one particularly preferred embodiment, the composite catalyst contains about 2.5 weight percent phosphorus, and the optimum phosphorus dosage within the disclosed ranges may be determined by one of ordinary skill in the art with a minimum of trial and error.

In a particularly preferred embodiment, the catalyst comprises ZSM-5 or ZSM-11 which has been steamed and/or treated with Mg, B, Si, or P to enhance its toluene alkylation selectivity for para-xylene to at least about 40 weight percent. Preferably, the catalyst has undergone prior treatment with a steam-containing atmosphere at a temperature between about 250° C. to about 1050° C. for between about 10 minutes and about 100 hours.

Referring now to the FIGURE, feed gas containing toluene and an alkylating agent passes under pressure through conduit 10, with the main flow being directed through the bottom inlet of reactor vessel 20 for distribution through grid plate 22 into the fluidization zone 24. Here the feed gas contacts the turbulent bed of finely divided catalyst particles. Reactor vessel 20 is shown provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is oxidatively regenerated by controlled contact with air or other regeneration gas at elevated temperature in a fluidized regeneration zone to remove carbonaceous deposits and restore acid activity. The catalyst particles are entrained in a lift gas and transported via riser tube 32 to a top portion of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40 and compressor 42 for return to the vessel with fresh oxidation gas via line 44 and as lift gas for the catalyst in riser 32.

Regenerated catalyst is passed to the main reactor 20 through conduit 46 provided with flow control valve 48. The regenerated catalyst may be lifted to the catalyst bed with pressurized feed gas through catalyst return riser conduit 50. Since the amount of regenerated catalysts passed to the reactor is relatively small, the temperature of the regenerated catalyst does not upset the temperature constraints of the reactor operations in significant amount. A series of sequentially connected cyclone separators 52, 54 are provided with diplegs 52A, 54A to return any entrained catalyst fines to the lower bed. These separators are positioned in an upper portion of the reactor vessel comprising dispersed catalyst phase 24. Filters, such as sintered metal plate filters, can be used alone or in conjunction with cyclones.

The product effluent separated from catalyst particles in the cyclone separating system is then withdrawn from the reactor vessel 20 through top gas outlet means 56. The recovered hydrocarbon product comprising aromatics, including para-xylene, is thereafter processed as required to separate the desired para-xylene from other reaction products or unconverted feed. With the inventive method, xylenes containing more than 90 wt % para-xylene can be recovered from the fluidized bed.

EXAMPLES

Example 1

A fluidizable composite catalyst containing ZSM-5 was calcined at 1000° F. for 3 hours to remove residual volatile material and then steamed at 1877° F. for 4 hours at 0 psig steam. The catalyst had a particle density of 1.3 g/cc and contained 5 wt % fines less than 40 microns. Toluene and methanol in a molar ratio of 4/1 was passed over 40 grams of catalyst in a fluidized bed of catalyst operated below the transport velocity at reaction conditions of 1105° F., 3.5 WHSV, and 20 psig. The reactor was operated in a batch mode with respect to catalyst. The fluid bed provided near complete conversion of methanol initially and over a period of ten hours the activity of the catalyst, as measured by conversion of toluene and methanol, declined (Table 1). The run was terminated after 15 hours-on-stream and the catalyst was analyzed to contain 6.3 wt. % coke.

TABLE 1

Example 1

| Reaction Conditions | | | |
|---|---|---|---|
| Temperature, F. | | 1105 | |
| Feed WHSV | | 3.5 | |
| Pressure, psig | | 21 | |
| Toluene/Methanol (mol) | | 4.1 | |
| Time On Stream, hrs. | 2 | 6 | 10 |
| Toluene Conversion, % | 14.6 | 13.1 | 10.5 |
| Methanol Conversion, % | 95.3 | 92.2 | 90.3 |

Example 2

Detailed analysis of the reaction product obtained from Example 1 at 6 hours-on-stream revealed a high content of xylenes with >90% selectivity to para-xylene (Table 2). The efficiency for alkylating toluene with methanol, termed 'methanol utilization', is defined as the moles of xylene produced per mole of methanol converted. In this Example, the methanol utilization was greater than 50% and the aromatic alkylation to desired xylenes was over 94% of the aromatic product.

TABLE 2

| | Example 2 | Example 4 |
|---|---|---|
| Reaction Conditions | | |
| Temperature, F. | 1105 | 1109 |
| Feed WHSV | 3.5 | 3.5 |
| Pressure, psig | 21 | 22 |
| Toluene/Methanol (mol) | 4.1 | 4.1 |
| Time-on-Stream, hrs | 6 | 6 |
| Reactor Product, wt. % | | |
| Water | 3.74 | 3.84 |
| MeOH | 0.61 | 0.59 |
| $C_4-$ | 1.07 | 0.97 |
| $C_5$+PON | 0.01 | 0.04 |
| Benzene | 0.10 | 0.09 |
| Toluene | 80.18 | 81.67 |
| Ethyl Benzene | 0.04 | 0.04 |
| p-Xylene | 12.55 | 11.33 |
| m-Xylene | 0.65 | 0.57 |
| o-Xylene | 0.35 | 0.30 |
| Ethyl Toluene | 0.14 | 0.14 |
| Trimethyl Benzene | 0.43 | 0.30 |
| $C_{10}$+Aromatics | 0.13 | 0.11 |
| Toluene Conversion, % | 13.1 | 11.4 |
| Methanol Conversion, % | 92.2 | 92.4 |
| Methanol Utilization, mol % | 57.0 | 51.2 |
| % Para in Xylenes, % | 92.6 | 92.9 |
| Xylenes/Aromatic Product, wt % | 94.2 | 94.6 |

Example 3

The aged catalyst from Example 1 was regenerated in an oxygen containing environment under conditions which simulate commercial regeneration. The catalyst was regenerated at 1025° F. and 3.1 psia $O_2$ for 2 hours. After regeneration the catalyst contained 0.02 wt. % coke.

Example 4

The regenerated catalyst from Example 3 was returned to the fluid-bed reactor in Example 1 and toluene and methanol in a 4/1 molar ratio was passed over the catalyst at 1105° F. at 3.5 WHSV and 20 psig. The activity of the catalyst was increased to above that of the aged (10 hour-on-stream) catalyst in Example 1 and the reaction product obtained had a high content of xylenes as shown in Table 2. The high selectivity to para-xylene and greater than 50% methanol utilization observed in Example 2 was maintained.

Example 5

In this Example, the effect of varying the flow regime in the fluid catalyst bed was investigated. The catalyst was the same as that employed in Example 1 and in one test (Run A) the bed was operated at a superficial velocity of 0.28 ft/sec at the grid inlet which was above the minimum slugging velocity for this reactor but less than the transport velocity. The minimum slugging velocity ($U_{ms}$) is the point at which the gas superficial velocity pushes slugs of solid up the bed at a rise velocity greater than the bubble rise velocity. In a second test (Run B) the bed was operated in a bubbling dense bed flow regime below the minimum slugging velocity. The results are summarized in Table 3, from which it will be seen that, surprisingly, the methanol utilization and para-xylene selectivity were significantly greater with fluid bed operating as a turbulent bed below the transport velocity. Also, an unexpected improvement in xylenes as a fraction of total aromatic product was achieved.

TABLE 3

| Run | A | B |
|---|---|---|
| Toluene/methanol (mol) | 4.1 | 4.1 |
| Temperature, F. | 1114 | 1115 |
| Pressure, psig | 20 | 20 |
| WHSV | 3.5 | 3.5 |
| Ums, ft/sec | 0.16 | 0.16 |
| U, ft/sec | 0.28 | 0.08 |
| Toluene conversion, % | 13.4 | 5.1 |
| Methanol conversion, % | 92.7 | 87.9 |
| Methanol utilization, mol % | 58 | 27 |
| P-xylene selectivity, % | 94 | 83 |
| Xylene yield, wt % | 15 | 6.7 |
| Xylene/Aromatic Product, wt % | 95.8 | 91.0 |

Example 6

In this Example the effect of varying the fines content of the catalyst was investigated with a fluid bed operating in the turbulent regime. The catalyst was similar to that of Example 1 but in one test (Run C) the fines content (<40 micron particles) was within the 5–35 wt % range of invention, whereas in a second test (Run D) the fines content the below the range of the invention. The results are summarized in Table 4, from which it will be seen that the methanol utilization and para-xylene yield were significantly greater when the fines content was within the range of the invention.

TABLE 4

| Run | C | D |
|---|---|---|
| Toluene/methanol (mol) | 2 | 2 |
| Temperature, F. | 1100 | 1093 |
| Pressure, psig | 20 | 21 |
| WHSV | 1.57 | 1.63 |
| Average particle size, micron | 71 | 112 |
| Fines (<40 micron), wt % | 13.5 | 0.2 |
| Toluene conversion, % | 30.3 | 26.6 |
| Methanol conversion, % | 99.2 | 93.4 |
| Methanol utilization, mol % | 61.3 | 56.3 |
| P-xylene selectivity, % | 89.5 | 89.5 |
| Xylene yield, wt % | 35 | 30.3 |
| Xylene/aromatic product, wt % | 95.5 | 95.2 |

What is claimed is:

1. A process for the selective production of para-xylene which comprises:

(a) providing, in a fluidized bed, a fluidizable catalyst comprising a microporous material having a Constraint index of from about 1 to about 12;

(b) controlling the relative concentration of catalyst particles having a major dimension of less than 40 microns at between about 5 and 35 weight percent, said catalyst particles having an apparent particle density of about 0.9 to 1.6 grams per cubic centimeter and a size range of about 1 to 150 microns, and an average catalyst particle size of about 20 to 100 microns;

(c) charging toluene and a methylating agent to said fluidized bed at a rate sufficient to maintain said fluidized bed in a turbulent sub-transport flow regime; and (d) reacting said toluene with said methylating agent and recovering para-xylene from said fluidized bed.

2. The process of claim 1 wherein said methylating agent is methanol, methylchloride, methylbromide, dimethylether or dimethylsulfide.

3. The process of claim 1 wherein the step of reacting toluene with a methylating agent is carried out at a temperature between about 300° C. and 750° C., a pressure of between about 101–7000 kPa (0–1000 psig), a weight hourly space velocity between about 0.5 and about 1000 employing a molar ratio of methylating agent to toluene of less than about 5.

4. The process of claim 3 wherein said temperature is between about 500° C. and 700° C.

5. The process of claim 1 wherein said microporous material is a zeolite characterized by a silica/alumina ratio in excess of 30.

6. The process of claim 1 wherein said microporous material is ZSM-5.

7. The process of claim 1 wherein said catalyst has undergone prior treatment with a steam-containing atmosphere at a temperature between about 250° C. to about 1050° C. for between about 10 minutes and about 100 hours.

8. The process of claim 1 wherein said catalyst contains phosphorus.

9. The process of claim 1 wherein said microporous material is composited with a binder selected from the group consisting of clay, silica, silica-alumina, silica-magnesia, silica-zirconia, silica-thoria, silica-beryllia, and silica-titania, silica-alumina-thoria, silica-alumina-zirconia, silica-alumina-magnesia, and silica-magnesia-zirconia.

10. A process for the selective production of para-xylene which comprises:

(a) providing, in a fluidized bed, a fluidizable catalyst comprising a microporous material having a Constraint index of from about 1 to about 12, the microporous material containing phosphorous and having undergone prior treatment with a steam-containing atmosphere at a temperature between about 250° C. to about 1050° C. for between about 10 minutes and about 100 hours;

(b) controlling the relative concentration of catalyst particles having a major dimension of less than 40 microns at between about 5 and 35 weight percent, said catalyst particles having an apparent particle density of about 0.9 to 1.6 grams per cubic centimeter and a size range of about 1 to 150 microns, and an average catalyst particle size of about 20 to 100 microns;

(c) charging toluene and a methylating agent selected from methanol, methylchloride, methylbromide, dimethylether and dimethylsulfide to said fluidized bed at a rate sufficient to maintain said fluidized bed in a turbulent sub-transport flow regime; and (d) reacting said toluene with said methylating agent and recovering xylenes containing more than 90 wt % para-xylene from said fluidized bed.

\* \* \* \* \*